United States Patent
Chapleo et al.

(10) Patent No.: US 8,497,280 B2
(45) Date of Patent: Jul. 30, 2013

(54) MEDICINAL COMPOSITIONS COMPRISING BUPRENORPHINE AND NALMEFENE

(75) Inventors: Christopher Bourne Chapleo, Hull (GB); Neil Hyde, Hull (GB)

(73) Assignee: RB Pharmaceuticals Limited, Slough, Berkshire (GB)

( * ) Notice: Subject to any disclaimer, the term of this patent is extended or adjusted under 35 U.S.C. 154(b) by 711 days.

(21) Appl. No.: 12/529,314

(22) PCT Filed: Feb. 15, 2008

(86) PCT No.: PCT/GB2008/000522
§ 371 (c)(1), (2), (4) Date: Jan. 11, 2010

(87) PCT Pub. No.: WO2008/104736
PCT Pub. Date: Sep. 4, 2008

(65) Prior Publication Data
US 2010/0152222 A1 Jun. 17, 2010

(30) Foreign Application Priority Data
Mar. 1, 2007 (GB) .................................. 0703933.2

(51) Int. Cl.
*A61K 31/44* (2006.01)

(52) U.S. Cl.
USPC ........................................... 514/279; 514/282

(58) Field of Classification Search
USPC .................................................... 514/279, 282
See application file for complete search history.

(56) References Cited

U.S. PATENT DOCUMENTS
2003/0004178 A1   1/2003  Chapleo

OTHER PUBLICATIONS
Combined Search and Examination Report of GB 0703933.2.
International Search Report of PCT/GB2008/000522.

*Primary Examiner* — Sreeni Padmanabhan
*Assistant Examiner* — Jody Karol
(74) *Attorney, Agent, or Firm* — Ryan A. Schneider; Troutman Sanders LLP

(57) ABSTRACT

An analgesic composition, in parenteral unit dosage form or in a unit dosage form suitable for delivery via the dermis or mucosa, comprises buprenorphine and an amount nalmefene such that the ratio by weight of buprenorphine to nalmefene delivered to or reaching the plasma of a patient is in the range 22.6:1 to 40:1. The analgesic action of the buprenorphine is potentiated by the low dose of nalmefene. Also provided are a method of treatment of pain and the use of nalmefene and buprenorphine for the manufacture of a medicament.

7 Claims, 1 Drawing Sheet

MEDICINAL COMPOSITIONS COMPRISING BUPRENORPHINE AND NALMEFENE

BENEFIT CLAIMS

This application is a US National Stage of International Application No. PCT/GB2008/000522, filed 15 Feb. 2008, which claims the benefit of GB 0703933.2, filed 1 Mar. 2007.

FIELD OF THE INVENTION

The present invention relates to medicinal compositions containing buprenorphine in combination with nalmefene; as well as to their use in the manufacture of such compositions and in clinical practice, as analgesics.

BACKGROUND OF THE INVENTION

Whilst opioids are particularly effective in the management of moderate to severe pain their use is limited by unpleasant and potentially dangerous adverse effects. Such adverse effects can include sedation, respiratory depression, nausea and gastrointestinal problems. Thus efforts have been made to minimise adverse effects.

There are many opioids and some produce more significant adverse effects than others. Accordingly, careful selection of the opioid employed in an analgesic composition may itself reduce the incidence and severity of adverse effects. One particularly suitable opioid is buprenorphine which has been shown to have both agonist (morphine-like) and antagonist properties without producing, significant physical dependence.

Buprenorphine (International Non-proprietary Name for N-cyclopropylmethyl-7[alpha]-[1-(S)-hydroxy-1,2,2-trimethyl-propyl]6,14-endoethano-6,7,8,14-tetrahydronororipavine) is a potent opiate partial agonist analgesic lacking the psychotomimetic effects found with other opiate analgesics. However, buprenorphine suffers from side effects typical of opiate agonists such as nausea and vomiting, constipation and respiratory depression in some patients, although there is a ceiling to its effects on respiratory depression as a direct consequence of its partial agonist properties.

Attempts have also been made to enhance the analgesic effect of opioids while minimising the incidence and severity of adverse effects by combining opioid treatment with other drugs.

One approach is the addition of a non-opioid analgesic to the opioid treatment. The rationale here is that lower levels of opioid should be required to achieve antinociception and thus there should be a reduction of adverse effects.

Another approach is the co-administration of an opioid agonist and low doses of an opioid antagonist. One such opioid antagonist is nalmefene (International Non-Proprietary Name for (5)-17-(cyclopropylmethyl)-4,5-epoxy-6-methylene-morphinan-3,14-diol).

In EP 1242087A it is disclosed that parenteral and sublingual dosage forms of buprenorphine are potentiated and enhanced by low doses of nalmefene. Based testing on rats, there is stated a suitable ratio by weight of buprenorphine to nalmefene of 12.5:1 to 22.5:1, preferably 15:1 to 20:1.

Human studies have now been carried out and have generated new findings for the combined use of buprenorphine, as opioid agonist, and nalmefene, as opioid antagonist. These new findings extend our understanding of the therapeutic doses which will give effective analgesia in humans.

According to a first aspect of the present invention there is provided an analgesic composition, in parenteral unit dosage form or in a unit dosage form suitable for delivery via the mucosa or dermis, the composition comprising buprenorphine and an amount of nalmefene such that the ratio by weight of buprenorphine to nalmefene delivered to or reaching the plasma of a patient is in the range 22.6:1 to 40:1.

It is believed that the analgesic action of buprenorphine is potentiated by the relatively small level of nalmefene.

It is to be understood that the terms buprenorphine and nalmefene as used herein are intended to cover simple related, pharmaceutical compounds such as esters, bases and salts, for example acid addition salts. Particularly preferred salts are the hydrochlorides. However the ratios and weights referred to herein refer to buprenorphine and nalmefene per se, not salts, bases or esters.

The term parenteral is intended to encompass administration of the compositions by any way other than through the alimentary tract.

The term mucosa or mucosal is intended to encompass any mucous membrane and includes oral mucosa, rectal mucosa, vaginal mucosa and nasal mucosa. The term dermal denotes non-mucosal skin.

Administration may take a few minutes. Preferably it takes place over a period of at least one minute, preferably at least two minutes, preferably at least three minutes. Preferably it takes place over a period of up to ten minutes, preferably up to seven minutes, preferably up to five minutes.

The unit dosage form for transdermal or transmucosal administration may, for example, be a tablet, film, spray, patch, rub-in composition or lozenge. Administration, which will be further described in the second aspect, may comprise the delivery of a medicament comprising buprenorphine and nalmefene, preferably in such a form.

Transdermal administration may encompass any mode of administration trough the dermis. Transmucosal administration may encompass any mode of administration trough the mucosa, and sites of administration may include, for example, vaginal and, rectal mucosa and, preferably, mucosa of the oral-nasal cavity, for example nasal, throat, buccal and, sublingual sites. Nasal and sublingual administration is especially preferred.

Preferably the defined ratio of buprenorphine to nalmefene is achieved within sixty minutes after administration means herein within sixty minutes after administration being completed, that is, preferably at some time within sixty minutes of administration being completed, the defined drug ratio in the plasma is achieved.

Preferred compositions comprise buprenorphine and nalmefene such that the ratio by weight of buprenorphine to nalmefene delivered to or reaching the plasma of the patient is at least X:1 (X to 1) where X is 23, preferably 24, preferably 25.

Preferred compositions comprise buprenorphine and nalmefene such that the ratio by weight of buprenorphine to nalmefene provided delivered to or reaching the plasma of the patient is no greater than Y:1 (Y to 1) where Y is 36, preferably 32, preferably 30.

Surprisingly, it has been found that even at the low levels of nalmefene to buprenorphine employed in the present invention the nalmefene is able to potentiate the agonist action of buprenorphine. Additionally, through the use of nalmefene adverse effects and/or misuse of buprenorphine may be minimised. A surprising finding is that ratios of buprenorphine to nalmefene of 25:1 or greater, for example 30:1 are particularly effective.

The composition may comprise a parental unit dosage form and the ratio of buprenorphine to nalmefene within the parenteral composition may be substantially the same as that produced in the plasma of a patient upon application. Thus the parenteral dosage form may comprise buprenorphine and nalmefene in any of the weight ratios stated above for the weight ratios in the plasma.

In a human being, as stated in EP 1242087B dosages of about 40 μg of buprenorphine per kilogram of body weight are suitably required to obtain satisfactory pain relief in the absence of potentiation. Thus for typical body weights of 50 to 80 kg, the buprenorphine dosage would be from 2 mg to 3.2 mg of buprenorphine per day. This would conveniently be administered as four unit doses.

The amounts of buprenorphine which are required to be effective in the compositions of the invention are less than the amounts which are required to be effective in the absence of the potentiating effects of nalmefene.

Importantly when equal doses of buprenorphine with and without the potentiating effect of nalmefene are compared, the magnitude and duration of analgesia achieved by the former compositions (i.e. also containing nalmefene), are markedly increased. Therefore the same analgesic performance can be achieved with a lower buprenorphine dose when combined with nalmefene. It is proposed that an increased analgesic effect can be achieved and/or reduced concentration of buprenorphine can be used, within or across the therapeutic range.

Suitably, unit doses of the compositions of the present invention (containing nalmefene) contain buprenorphine in an amount which is below that required to obtain, corresponding pain relief in a unit dose of buprenorphine without nalmefene.

Suitably, the compositions of the present invention comprise at least 10 μg of buprenorphine per unit dose, preferably at least 15 μg, preferably at least 20 μg, preferably at least 30 μg, and most preferably at least 40 μg. These values reflect the benefit of the invention in achieving analgesia at low dosages.

Suitably, the compositions of the present invention may contain any amount of buprenorphine, up to the upper end of conventional clinical practice. Suitably, they may contain up to up to 32 mg buprenorphine per unit dose, preferably up to 16 mg, preferably up to 8 mg, preferably up to 4 mg, preferably up to 2 mg, preferably up to 1 mg, preferably up to 600 μg, preferably up to 400 μg, preferably up to 200 μg, preferably up to 160 μg, and most preferably up to 100 μg.

Suitably, in accordance with the present invention, a patient is administered at least 0.25 μg of buprenorphine per kg (of body weight) per 24 hours. Preferably the amount is at least 0.5 μg, preferably at least 1 μg, preferably at least 1.5 μg and most preferably at least 2 μg.

Suitably, in accordance with the present invention, a patient is administered up to 640 μg of buprenorphine per kg of body weight per 24 hours. Preferably the amount is up to 320 μg, preferably up to 160 μg, preferably up to 80 μg, preferably up to 40 μg, preferably up to 20 μg, preferably up to 16 μg, and preferably up to 12 μg. Most preferably the amount is not greater than 8 μg.

Suitably by use of compositions of the present invention the amount of buprenorphine administered to a patient for the purpose of achieving relief from pain is at least 40 μg per 24 hours, preferably at least 60 μg, preferably at least 80 μg, preferably at least 120 μg, and most preferably at least 160 μg.

Suitably by use of compositions of the present invention the amount of buprenorphine administered to a patient for the purpose of achieving relief from pain is up to 32 mg, preferably up to 16 mg, preferably up to 8 mg, preferably up to 4 mg, preferably up to 2 mg, preferably up to 1 mg, preferably up to 800 μg, preferably up to 600 μg, preferably up to 400 μg, preferably up to 200 μg, preferably up to 160 μg, preferably up to 100 μg.

Suitably, a composition containing nalmefene comprises from 0.4 μg to 24 μg of nalmefene per unit dose, preferably 0.6 to 12 μg, most preferably 0.8 to 6 μg.

Suitably the amount of nalmefene administered is between 0.01 and 0.8 μg per kg of body weight per 24 hours. Preferably the amount is at least 0.02 μg, preferably at least 0.03 μg. Preferably the amount is not greater than 0.4 μg, preferably not greater than 0.4 μg, preferably not greater than 0.05 μg. Preferably it is not greater than 0.04 μg.

Suitably the amount of nalmefene administered is in the range from 1 μg to 80 μg per 24 hours, preferably 2 to 36 μg, preferably 3 to 20 μg, preferably 4 to 10 μg.

References above to the amounts of compounds which may be administered to a patient are with reference to an adult patient.

Whatever the absolute amounts of buprenorphine and nalmefene administered, the definition(s) stated herein of the ratio of buprenorphine to nalmefene must be satisfied.

It is preferable to formulate the compositions in unit dosage forms i.e. physically discrete units containing the appropriate amounts of buprenorphine and nalmefene, together with pharmaceutically acceptable diluents and/or carriers. Such unit dosage forms for parenteral administration are suitably in the form of ampoules. For delivery via the mucosa may for example be in the form of sublingual tablets, films or lozenges.

Compositions of the invention may contain a buffer system, for example an organic acid and a salt thereof, such as citric acid and sodium citrate.

Compositions in the form of sublingual dosage forms suitably contain soluble excipients selected from materials such as lactose, mannitol, dextrose, sucrose or mixtures thereof. They suitably also contain granulating and disintegrating agents selected from materials such as starch, binding agents such as povidone or hydroxypropyl-methyl cellulose and lubricating agents such as magnesium stearate.

Compositions intended for parenteral administration may comprise an isotonic solution of buprenorphine and nalmefene in sterile water. Conveniently the solution may be made isotonic by use of dextrose and sterilised by autoclaving or by filtration through a membrane filter. The compositions may be administered intramuscularly, intradermally, intraperitonealy, intravenously, intraarterially, subcutaneously or by the epidural route.

The compositions for parenteral administration, or for delivery via the mucosa, such as by sublingual administration, as detailed above, may be prepared by manufacturing techniques which are well known to those skilled in the art.

According to a second aspect the present invention there is provided a method for the treatment of pain in a human patient, which method comprises the administration to a human patient, by a parenteral or dermal or mucosal route, of buprenorphine and nalmefene such that the ratio by weight of buprenorphine to nalmefene delivered to or reaching the plasma of a patient is in the range 22.6:1 to 40:1.

Preferred ratios of buprenorphine to nalmefene delivered to or reaching plasma of the patient are as defined above with respect to the first aspect.

Suitably, the method comprises delivery via the mucosa. The method may comprise delivery in a sublingual unit dosage form.

Suitably, the method comprises the administration of buprenorphine and an amount of nalmefene for the purpose of potentiating the analgesic action of the buprenorphine and in particular to optimising the balance between the analgesic action of the buprenorphine and the anti-abuse presence of the nalmefene. It will be appreciated that this balance is extremely important. The medicament must be a potent analgesic for it to fulfil its intended function. At the same time in the present day it is vitally important that opioid medicaments discourage abuse by addicts. It is believed that the present invention is extremely effective in these respects.

Separate, administration of buprenorphine and or nalmefene is not excluded in the method. Suitably, however, the method comprises administering a composition comprising buprenorphine and nalmefene, to a human. Suitably, the method employs a composition according to the first aspect. The definitions given above in relation to the first aspect apply to the second aspect, noting however that the buprenorphine and nalmefene may in principle be administered separately in the second aspect.

Suitably, the method comprises administering to the human or animal from 0.25 µg to 20 µg per kilogram of body weight of buprenorphine per day.

The method may comprise administering a dose of buprenorphine which would, if administered alone, produce minimal or no antinociception. The method may comprise administering to the human amounts of buprenorphine and nalmefene as stated above in relation to the first aspect of the invention.

The method may comprise any feature as described in relation to the first aspect.

According to a third aspect of the present invention there is provided the use of buprenorphine and nalmefene in the manufacture of a medicament for the treatment of pain, wherein the buprenorphine and nalmefene are used in an amount such that the medicament is delivered to a patient at, or reaches in the plasma of a patient, a ratio by weight in the range: 22.6:1 to 40:1.

Suitably this aspect comprises the use of buprenorphine and of nalmefene in the manufacture of a medicament for the treatment of pain, wherein buprenorphine is used for its analgesic effect, but at lower level than would be needed, for a given analgesic effect against a given pain in a given patient, in the absence of nalmefene. Thus the nalmefene potentiates the analgesic effect of buprenorphine. Further, it renders the medicament less attractive to drug addicts.

The use of buprenorphine and of nalmefene in the manufacture of a medicament according to the third aspect may comprise any feature as described in relation to the first or second aspect.

Suitably, the use of buprenorphine and of nalmefene in the manufacture of a medicament comprises the manufacture of a medicament comprising a composition according to the first aspect. However the use of buprenorphine and of nalmefene in the manufacture of a medicament having two dosage units, containing buprenorphine and nalmefene respectively, is not excluded.

BRIEF DESCRIPTION OF THE DRAWINGS

The present invention will now be illustrated by way of example with reference to the accompanying drawings in which.

DETAILED DESCRIPTION OF PREFERRED EMBODIMENTS

Methods

Nociceptive Testing

Figure 1:
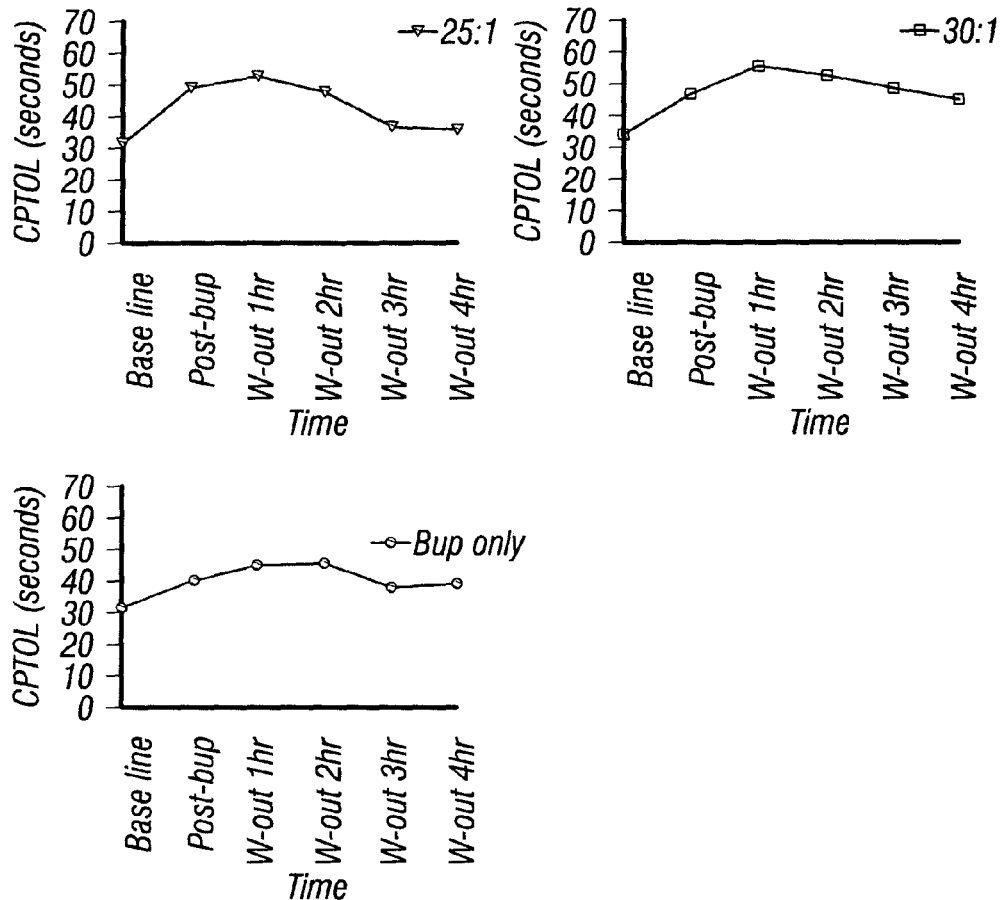
FIG. 1 comprises graphs showing pain tolerance for buprenorphine and combinations with nalmefene.

The cold pressor (CP) test was used to assess antinociception of buprenorphine and buprenorphine and nalmefene or nalmefene combinations. The compound forms were buprenorphine HCl and nalmefene HCl dihydrate. The CP test utilised two plastic cylindrical containers, one of which was filled with warm water and the other with a combination of water and crushed ice to achieve a "slushy" consistency. The subject immersed the non-dominant forearm and hand into the warm water for exactly 2 minutes. At 1 minute 45 seconds, a blood pressure cuff on the immersed arm was inflated to a pressure 20 mm Hg below the diastolic blood pressure. The blood pressure cuff minimised the role of blood flow in determining the reaction to cold. At exactly 2 minutes, the forearm was transferred from the warm water to the cold water bath. The subject's eyes were covered for the entire procedure to minimise distraction and cues for time. Upon immersion of the limb in the cold water bath, subjects were asked to indicate when they first experienced pain (pain threshold, CPTHR), then asked to leave their arm submerged until they can no longer tolerate the pain (pain tolerance, CPTOL). Pain threshold and tolerance times were recorded in seconds from immersion in cold. An undisclosed cut-off of 180 seconds was imposed, after which time pain tolerance can no longer be accurately assessed due to numbness. Pain tolerance (CPTOL) is the reported pain response parameter in the current investigations.

For the present tests nociceptive testing was conducted in the same environment, with minimal background noise, audible voices and no clock with audible ticking. Ambient room temperature and lighting was consistent. At no time did the experimenter discuss with the subject his/her performance on the test, or answer any questions related to the average pain tolerance time or any previous results.

Screening

Before testing subjects were screened according to the inclusion and exclusion criteria based upon such factors as previous medical conditions and drug abuse.

Test Procedure

Suitable screened subjects were tested according to the following procedure. Subjects provided a urine sample upon arrival on the day of testing, which was tested for drugs of abuse (opioids, cannabinoids, benzodiazepines and sympathomimetic amines) and, for female subjects, pregnancy. A 22 gauge indwelling venous catheter was inserted into the best available forearm vein on each arm (above the CP immersion line for the non-dominant arm). A male luer lock adaptor injection site was attached to each catheter. One catheter was used for blood sampling throughout the testing day, and the other for infusions. The participant was then connected to a monitor, which was set to continuously monitor physiological parameters for the duration of the testing session.

On each testing day, subjects received a 30 minute unblinded intravenous infusion of saline, followed by one or more 30 minute drug (or placebo) infusions. The purpose of the initial saline infusion was two-fold: to establish whether any changes in pain or physiological parameters would occur as a response to the infusion process itself, and to ensure that there was no obstruction to venous access via the catheter and the infusion pump was operating correctly.

Infusions were administered using a Syringe Pump. Drugs and saline were prepared in 30 ml BD Plastipak syringes.

Infusions were run at a rate of 20 ml per hour for 30 minutes. Each syringe was attached to a minimum volume extension set (150 cm tubing, female luer lock, male luer lock, 0.5 mL/30 cm). The male luer lock was attached to a lever lock cannula. The extension set was primed with the drug/saline, and inserted into the injection site. In buprenorphine:antagonist ratio studies, BUP and antagonist were administered simultaneously. For the simultaneous infusion of two drugs (via one cannula), a Y-type catheter extension set with two injection sites was attached to the catheter, and the lever lock cannulas (connected via the minimum volume extension set to each syringe) were inserted in each of the injection sites.

Testing sessions were conducted on numerous occasions during each testing day. Each testing session consisted of the following measures in the order listed: nausea and sedation recorded, blood sample taken, physiological parameters recorded (pulse, oxygen saturation and blood pressure), nociceptive testing (as detailed above) completed, and respiration recorded (breaths per minute counted for one full minute during warm water component of CP).

Testing sessions were conducted at set intervals throughout each testing day. These were as follows: 1. Prior to the commencement of infusions; 2. Twenty minutes after the commencement of the 30 minute saline infusion; 3. Twenty minutes after the commencement of the 30 minute drug infusion, and hourly following the cessation of the (last) drug infusion. This is referred to as the washout period. The purpose of conducting the testing session 20 minutes after commencing each 30 minute infusion was to allow time for the testing to be completed before starting the subsequent infusion.

Comparison of Results

As baseline values were different between conditions, CPTOL data were expressed as percent change from baseline in order to compare the effect associated with different drug combinations. Each participant's response at each time point for each condition was expressed as a percent change from baseline response according to the equation below. Data are expressed as the mean (±SEM) of these values at each post-drug testing session for each condition.

$$\frac{\text{Post-drug latency} - \text{baseline latency}}{\text{baseline latency}} * 100$$

This provided a value for percentage change CPTOL.

EXAMPLES

Example 1

Four healthy Caucasian participants (2 males, 2 females) ranging in age from 19 to 27 years (Mean±SEM, 21.7±1.8 years) were enrolled in the study. Mean body weight was 77.5 kg (±9.1, range 63-104 kg) and mean CPTOL at screening was 38.7 seconds (±5.6, range 25-52 seconds). There were no significant differences between males and females in terms of age (p=0.277) or CPTOL at screening (p=0.974).

Subjects were administered buprenorphine and nalmefene in a ratio of 25:1 by IV infusion with buprenorphine administered at a dose of 0.5 µg/kg body weight. The CPTOL results are presented in FIG. 5. No adverse effects causing concern were noted.

Example 2

Comparative

As a comparative example the same subjects from Example 1 were administered, on a separate day, buprenorphine and saline (referred to subsequently as "BUP only") by IV infusion. Buprenorphine was again administered at a dose of 0.5 µg/kg body weight. The CPTOL results are presented in FIG. 5.

Example 3

The same subjects from Example 1 were administered, on a separate day, buprenorphine and nalmefene in a ratio of 30:1 by IV infusion with buprenorphine administered at a dose of 0.5 µg/kg body weight. The CPTOL results are presented in FIG. 1. No adverse effects causing concern were noted.

Comparison of Examples 4-6

Figure 2:
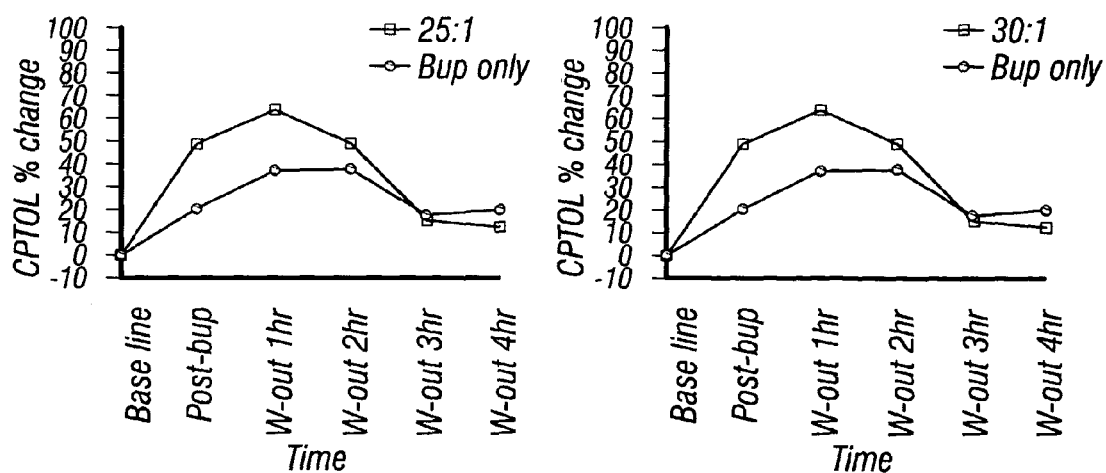
FIG. 2 comprises comparative graphs.

The percentage change for CPTOL from the baseline was calculated for Examples 1, 2 and 3 and the results are presented in FIG. 2. It may be seen that there was a marked benefit of the buprenorphine and nalmefene combinations compared to buprenorphine alone.

Example 7

Buprenorphine/Nalmefene Parenteral Composition

A parenteral formulation having the following composition:

|  | mg/ml. |
| --- | --- |
| Buprenorphine as HCl salt | 0.01 |
| Nalmefene as HCl salt | 0.004 |
| Anhydrous dextrose | 52.0 |
| Hydrochloric acid | to pH 4.0 |
| Water for injection | to 1.0 ml | was prepared by dissolving dextrose, buprenorphine hydrochloride and nalmefene or nalmefene hydrochloride in that order with stirring, in about 95% batch volume of water for injection. The acidity of the solution was adjusted to pH 4.0 by the addition of 0.1M hydrochloric acid, and the solution was made up to volume with water for injection. The solution was filtered through, a membrane filter and transferred to sterilised 2 ml glass ampoules containing 2 ml of the solution. The ampoules were sealed and the product sterilised by autoclaving.

What is claimed is:

1. An analgesic composition, in parenteral unit dosage form or in a unit dosage form suitable for delivery via the mucosa or dermis, the composition comprising buprenorphine and an amount of nalmefene such that the ratio by weight of buprenorphine to nalmefene delivered to, or reaching the plasma of, a patient is in the range 23:1 to 40:1.

2. A composition as claimed in claim 1, wherein the amount of buprenorphine in the unit dosage form is from 10 µg to 8 mg.

3. A composition as claimed in claim 1, wherein the composition contains buprenorphine and nalmefene in a ratio of 23:1 to 36:1.

4. A method for the treatment of pain in a human patient, which method comprises the administration to a human patient, by a parenteral or dermal or mucosal route, of buprenorphine and nalmefene such that the ratio by weight of buprenorphine to nalmefene delivered to, or reaching the plasma of, a patient is in the range 23:1 to 40:1 for buprenorphine: nalmefene.

5. A method as claimed in claim 4, wherein the administration of buprenorphine is in the range 0.25 to 640 μg per kg of body weight per 24 hours.

6. A composition as claimed in claim 1, wherein the composition contains buprenorphine and nalmefene in a ratio of 24:1 to 32:1.

7. A composition as claimed in claim 1, wherein the composition contains buprenorphine and nalmefene in a ratio of 25:1 to 30:1.

* * * * *